United States Patent [19]

Adamczyk

[11] Patent Number: 4,922,939
[45] Date of Patent: May 8, 1990

[54] DENTAL CLEANING APPARATUS

[76] Inventor: Henry Adamczyk, 2 Windsor Ave., Scullville, N.J. 08330

[21] Appl. No.: 151,211

[22] Filed: Feb. 1, 1988

[51] Int. Cl.$^5$ .................................................. B08B 3/06
[52] U.S. Cl. ...................... 134/140; 134/154; 134/162; 134/182; 134/200
[58] Field of Search ............... 134/140, 143, 154, 162, 134/163, 182, 192, 200, 113

[56] References Cited

U.S. PATENT DOCUMENTS

| 84,524 | 12/1868 | Wood et al. | 366/306 X |
|---|---|---|---|
| 551,377 | 12/1895 | Haggard | 134/162 X |
| 556,358 | 3/1896 | Maxfield | 134/163 X |
| 556,604 | 3/1896 | Willie | 134/163 |
| 703,460 | 7/1902 | Pettengill | 134/162 X |
| 716,566 | 12/1902 | Meeker | 366/306 X |
| 954,615 | 4/1910 | Cram | 134/163 X |
| 962,839 | 6/1910 | Holt | 134/143 |
| 1,348,322 | 8/1920 | Rohne | 134/182 |
| 1,388,431 | 8/1921 | Hock | 134/154 |
| 1,678,037 | 7/1928 | Dunn | 134/182 |
| 1,907,366 | 5/1933 | Regero | 134/154 |
| 1,934,019 | 11/1933 | Thew | 134/182 |
| 2,128,921 | 9/1938 | Draeger | 134/187 |
| 2,275,411 | 3/1942 | Ashe | 134/182 |
| 2,545,914 | 3/1951 | Boucher | 134/140 X |
| 2,566,819 | 9/1951 | Baltsois | 134/140 X |
| 3,041,212 | 6/1962 | Booth | 134/154 X |
| 4,582,076 | 4/1986 | Prat | 134/113 X |

Primary Examiner—Frankie L. Stinson
Attorney, Agent, or Firm—Chen Patents

[57] ABSTRACT

A cleaning apparatus for dentures has a container for holding cleaning fluid. Within the container there is rigidly attached a spacer which consists of a plurality of L-shaped thin baffles and a center. A basket for holding the denture has a vertical side wall with slots, each slot being provided with a vane. The bottom of the basket also has slots and vanes. The basket is attached to its cover which in turn is connected to the shaft of an electric motor, the basket then being immersed in the cleaning fluid in the container. The basket and its contents are spun rapidly in the cleaning fluid, causing turbulence in the cleaning fluid and circulation of the cleaning fluid through the slots of the basket, which clean the denture placed therein.

10 Claims, 1 Drawing Sheet

DENTAL CLEANING APPARATUS

BACKGROUND OF THE INVENTION

1. Field of the Invention

This invention relates generally to an apparatus for cleaning dentures.

2. Prior Art Discussion

The daily cleaning of dentures is conventionally accomplished by simply soaking the dentures in a cleaning fluid. This method of cleaning is not effective in removing stains from the dentures or food particles from the crevices between the teeth because the cleaning fluid is stagnant. More elaborate denture cleaning methods employ supersonic vibrations. These methods are expensive and require specific cleaning solutions.

U.S. No. 4,007,751 discloses an apparatus for washing fruit or vegetables. It consists of a vessel with a cover. A removable basket having a lattice-type of wall for holding the foodstuff to be washed is placed in the vessel and tightly closed by a disk attached to the underside of the cover. Within the cover, there is provided a mechanism for manually rotating the basket for agitation so as to distribute the wash water over the foodstuff through an opening on the cover a plurality of holes on the disk.

U.S. No. 2,706,992, U.S. No. 2,416,475 and U.S. No. 3,074,773 are all related to cleaning devices for watch parts. Containers made of wire mesh hold the watch parts. They are removably attached to a cover. An electrical agitator is also provided. None of this apparatus is suitable for cleaning dentures although it superficially resembles the apparatus of the present invention. Therefore there is a need for a convenient yet efficient device for cleaning dentures.

The objective of the present invention is to provide a simple, inexpensive and effective denture cleaning device. A further objective is to provide a new method for cleaning dentures.

SUMMARY OF THE INVENTION

This invention relates to a simple and effective cleaning device for dentures. The cleaning device comprises a bowl-shaped container having a spacer molded inside the container to define an interior space; a basket with slots and vanes on its side wall holding the denture to be cleaned, said basket being removably attached to a cover and placed in the container, where cleaning fluid is provided; and means for rotating the basket, such as an electric motor.

DESCRIPTION OF PREFERRED EMBODIMENTS

Figure 1:
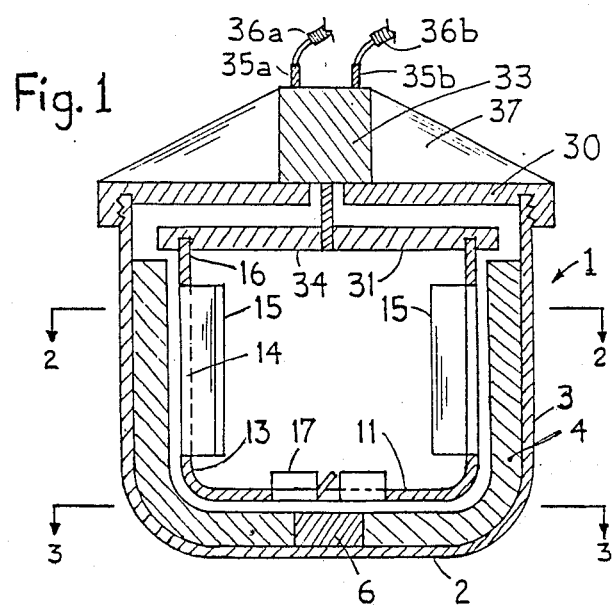
FIG. 1 shows a vertical cross section of the apparatus in accordance with the invention.
Figure 2:
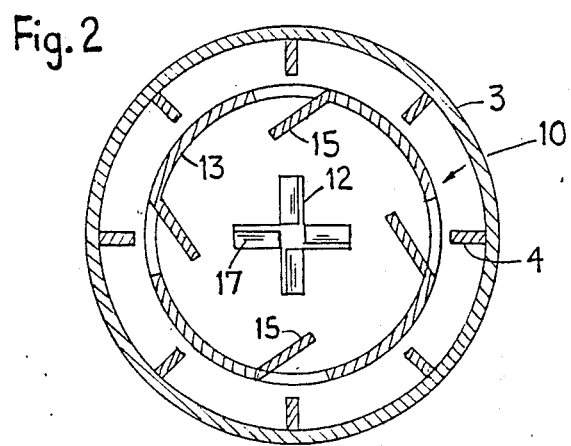
FIG. 2 shows a horizontal cross section of the apparatus in plane 2—2.
Figure 3:
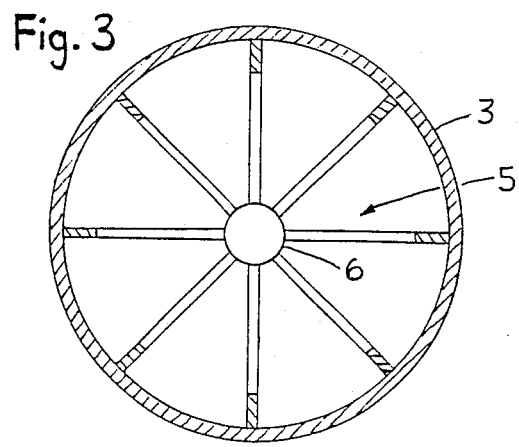
FIG. 3 shows a horizontal cross section of the apparatus in plane 3—3.

As shown in FIG. 1, a bowl-shaped container 1, has a flat bottom 2, a cylindrical side wall 3, and a circular container cover 30. Within the container, there is affixed a spacer 5, as best seen in FIG. 3, having a plurality of L-shaped baffles 4 radiating from a center 6. The center 6 may be a flat circular plastic disk. The baffles 4 are a plurality of thin L-shaped plastic ribs, rigidly attached at their inner ends to the center 6 and the outer edge of each baffle may be rigidly attached to the bottom 2 and the inside of the side wall 3 of the container. The baffles are evenly spaced around the periphery of the inside of the side wall 3, defining an interior space. Their height is about three-quarters of that of the side wall 3 of the container 1. Alternatively, the baffles may be rigidly held by the center without being individually affixed to the side wall 3. The spacer 5, being thus rigidly attached to the bottom 2 and in alignment with the side wall 3 of the container, forms an integral unit with the container. The container and the spacer are preferably made of hard clear plastic.

There is further provided a cylindrical basket 10, also preferably made of hard clear plastic, with diameter and height such that said basket fits within the interior space defined by the space 5 with approximately $\frac{1}{4}''$ vertical and radial clearances from the spacer. The basket 10 comprises a flat bottom 11 which has a plurality of slots, 12, preferably in form of a cross, which allow cleaning fluid to circulate through the basket 10. The basket 10 further comprises a side wall 13 having a plurality of evenly spaced elongated slots 14, each of which has a vertical vane 15 attached to one longitudinal side thereof, extending inwardly toward the interior of the basket 10, preferably at an acute angle with respect to a tangent to the periphery of the basket, such that cleaning fluid is pumped in a predetermined direction as the basket rotates as will be explained hereinafter. The length of the slots 14 and vanes 15 is approximately equal to the height of the side wall 13 of the basket 10. There are furthermore provided vanes 17 each attached to one of the longitudinal sides of the slots 12 and protruding towards the interior of the basket.

A peripheral collar 16 is provided at the upper edge of the side wall 13 of the basket. At the outer face of the collar 16, there is provided known means for attachment to a basket cover 31, such as a threaded, snap-on or bayonet closure. Said basket cover has matching means for attachment to the collar 16.

As shown in FIG. 1, the container cover 30 has a diameter commensurate with the top opening of the container 1. It is removably attached to the top edge of the wall 3 of the container 1 by known means such as bayonet or threaded closures.

On the upper surface of the container cover 30 at its center, there is affixed an electric motor 33. As shown in FIG. 1, the motor is enclosed in a housing, which in turn is buttressed by four brackets 37. The brackets are rigidly affixed on to the coveaar 30. It is to be understood that the motor may be affixed to the container cover by other conventional means.

The motor shaft 34 passes through an opening at the center of the container cover 30. It is firmly and concentrically attached to the basket cover 31. When the electric motor 33 is activated, the basket cover 31 and the basket 10 attached thereto thus rotate, as further discussed below.

The electric motor may be a low-voltage direct-current or alternating current motor, appropriate electrical power input being provided to the motor terminals 35a and 35b via wires 36a and 36b by known means. An AC adapter may be used to convert 120 volt AC power to a 3-9 volts DC.

In operation, the basket 10 holding the denture to be cleaned is attached to the basket cover 31. The container 1 is then filled about three quarters full with cleaning fluid and the container cover 30 is secured to the container 1, whereby the basket 10 and its contents are immersed in the cleaning fluid, clearing the spacer 5 including its components—the center 6 and the baffles 4, by approximately ¼" vertically and radially. When the motor is activated, the shaft rotates the basket cover 31, thereby rotating the basket 10 in the cleaning fluid.

The cleaning fluid placed in the container is agitated by the rotation of the basket, and the vanes 15 on the side wall 13 of the basket 10 in conjunction with the vanes 17 exert a pumping effect which causes the cleaning fluid to circulate vigorously and tortuously through the slots 14 and 12 in the side wall 13 and bottom 11 of the basket 10 into the interior of the basket, past the denture to be cleaned, and out of the basket via the apertures 12 in its bottom wall 11, into the annular space surrounding the basket 10 in the container 1. The baffles 4 prevent the cleaning fluid from swirling and forming a vortex which would interfere with the pumping action induced by the vanes 15 and 17 and the baffles in conjunction with the slots of the basket 10.

In an alternate configuration of this invention, the orientation of the vanes 15 and the rotation of the basket 10 are such that the flow of cleaning fluid is in the opposite direction to that described above. Cleaning fluid will ester the basket via the slots 12 in the bottom 11 of the basket 10, flow past the dentures to be cleaned, and exit from the basket 10 via the slots 14 in the side wall 13 of the basket 10, into the annular space surrounding the basket 10 in the container 1.

It should be apparent that the agitation and vigorous circulation of the cleaning fluid through the basket promotes the effective cleaning of the denture placed therein.

As a convenience to the user of the denture cleaning apparatus of this invention, an electrically operated clock timer may be installed on the container cover to turn off the motor 33 after a predetermined length of time, or to remind the user by a bell or a buzzer when cleaning has taken place for a predermined length of time.

It will be understood that various changes could be made in the apparatus of this invention without departing from the scope of said invention as defined by the following claims. The invention may be practiced otherwise than as particularly described.

I claim:

1. A denture cleaning apparatus comprising:
   a. a container for holding cleaning fluid, having a first bottom, a first side wall and container cover;
   b. a spacer having a plurality of L-shaped baffles affixed to the inside of the container along the side wall and bottom of said container and defining an interior space, a basket for holding the denture disposed within said interior space said basket having a second bottom with a plurality of slots and a second side wall with a plurality of evenly spaced elongated slots having a length about the height of the second side wall, and a plurality of vertical vanes attached along one longitudinal side of each of said slots, extending inwardly into the basket; and means for removably attaching said basket to a basket cover; and,
   c. means mounted on the container cover, firmly connected to the basket cover, for supporting and rotating the basket within said interior space of the container including an electric motor having a rotating shaft, said shaft concentrically passing through the container cover and the basket cover, said shaft being firmly connected to the basket cover, whereby the cleaning fluid is agitated and caused to circulate tortuously through the basket via the slots, cleaning the denture placed therein.

2. The apparatus of claim 1 wherein the L-shaped baffles radiate from a center, and are rigidly attached the the first bottom and said baffles being in alignment with the inside of the container.

3. The apparatus in accordance with claim 1 wherein the means for attaching the basket are screw threads.

4. The apparatus in accordance with claim 1 wherein the means for attaching the basket to its cover is a snap-on closure.

5. The apparatus in accordance with claim 1 wherein the means for attaching the basket to the basket cover is a bayonet closure.

6. The apparatus of claim 1 wherein the container is bowl-shaped and the first side wall is cylindrical.

7. The apparatus of claim 1 wherein said container, basket and spacer are made of hard plastic.

8. A denture cleaning apparatus comprising:
   a. a container for holding cleaning fluid having a first bottom, a first side wall, and a container cover;
   b. a spacer having a plurality of thin L-shaped baffles, radiating from a center, rigidly attached along the first bottom and the first side wall, inside said container, defining an interior space;
   c. a basket for holding a denture within said interior space, said basket having a second bottom with a plurality of slots; and a second side wall with a plurality of evenly spaced elongated slots, and a plurality of vertical vanes attached along one longitudinal side of each of said slots, extending inwardly into the basket; and said basket being removably attached to a basket cover; and
   d. an electric motor having a rotating shaft, centrally mounted on the container cover, said shaft passing through the container cover and being firmly connected to the basket cover, for supporting and rotating rotating the basket within the interior space of the container, whereby the cleaning fluid is agitated and caused to circulate tortuously through the basket via the slots cleaning the denture placed therein.

9. The apparatus of claim 8 further comprising a plurality of horizontal vanes attached to one of the longitudinal sides of the slots on the second bottom and said slots on the second bottom being in the form of a cross.

10. The apparatus of claim 8 further comprising an electric clock timer, disposed on the container cover for setting a predetermined cleaning time.

* * * * *